United States Patent
Yamada et al.

(10) Patent No.: US 12,070,067 B2
(45) Date of Patent: Aug. 27, 2024

(54) ASPIRATOR CARTRIDGE

(71) Applicant: Japan Tobacco Inc., Tokyo (JP)

(72) Inventors: Manabu Yamada, Tokyo (JP); Yutaka Kaihatsu, Tokyo (JP); Kentaro Matsuda, Tokyo (JP)

(73) Assignee: JAPAN TOBACCO INC., Tokyo (JP)

( * ) Notice: Subject to any disclaimer, the term of this patent is extended or adjusted under 35 U.S.C. 154(b) by 537 days.

(21) Appl. No.: 17/377,900

(22) Filed: Jul. 16, 2021

(65) Prior Publication Data
US 2021/0337873 A1    Nov. 4, 2021

Related U.S. Application Data

(63) Continuation of application No. PCT/JP2019/004868, filed on Feb. 12, 2019.

(51) Int. Cl.
| | | |
|---|---|---|
| A24F 40/40 | (2020.01) | |
| A24F 40/10 | (2020.01) | |
| A24F 40/42 | (2020.01) | |
| A24F 40/46 | (2020.01) | |
| H05B 3/22 | (2006.01) | |

(52) U.S. Cl.
CPC ............. *A24F 40/46* (2020.01); *A24F 40/10* (2020.01); *A24F 40/42* (2020.01); *H05B 3/22* (2013.01)

(58) Field of Classification Search
CPC ........... A24F 40/46; A24F 40/10; A24F 40/42
See application file for complete search history.

(56) References Cited

U.S. PATENT DOCUMENTS

| | | | | |
|---|---|---|---|---|
| 8,528,569 | B1* | 9/2013 | Newton | A61M 15/06 |
| | | | | 131/194 |
| 9,532,597 | B2* | 1/2017 | Tucker | A24F 40/42 |
| 9,918,495 | B2* | 3/2018 | DePiano | F22B 1/282 |
| 9,955,726 | B2* | 5/2018 | Brinkley | F22B 1/284 |
| 11,172,709 | B2* | 11/2021 | Watanabe | A24F 40/46 |
| 11,178,910 | B2* | 11/2021 | Kim | A24B 15/16 |
| 11,871,792 | B2* | 1/2024 | Kane | A24F 40/485 |
| 2016/0286864 | A1* | 10/2016 | Lin | A24F 40/485 |
| 2019/0046745 | A1* | 2/2019 | Nettenstrom | A61M 11/042 |
| 2021/0127742 | A1 | 5/2021 | Kim et al. | |

FOREIGN PATENT DOCUMENTS

WO    WO 2018/208078 A2    11/2018

OTHER PUBLICATIONS

Extended European Search Report for European Application No. 19915079.8, dated Sep. 12, 2022.
International Search Report (PCT/ISA/210) issued in PCT/JP2019/004868, dated Apr. 23, 2019.

* cited by examiner

*Primary Examiner* — Harshad C Patel
(74) *Attorney, Agent, or Firm* — Birch, Stewart, Kolasch & Birch, LLP

(57) ABSTRACT

An aspirator cartridge and an aspirator have new structures. An aspirator cartridge includes a heater unit configured to atomize a liquid in order to generate an aerosol. The heater unit includes: a liquid holding member that has a first surface and a second surface facing the first surface; a heater that comes in contact with the first surface of the liquid holding member; and a support member that supports the second surface of the liquid holding member and is softer than the liquid holding member.

11 Claims, 15 Drawing Sheets

ASPIRATOR CARTRIDGE

CROSS REFERENCE TO RELATED APPLICATIONS

This application is a Continuation of PCT International Application No. PCT/JP2019/004868, filed on Feb. 12, 2019, which is hereby expressly incorporated by reference into the present application.

TECHNICAL FIELD

The present disclosure relates to a cartridge for an inhaler.

BACKGROUND ART

Flavor inhalers for inhaling flavor without burning a material have been known. As such flavor inhalers, for example, electronic cigarettes are known. Such an electronic cigarette supplies aerosol generated by atomizing an aerosol-forming material containing a flavor such as nicotine to a mouth of a user, or causes aerosol generated by atomizing an aerosol-forming material that does not contain a flavor such as nicotine to pass through a flavor source (for example, a tobacco source) and then supplies the aerosol to the mouth of the user.

Some electronic cigarettes include a tank or reservoir that accommodates a liquid for generating aerosol, and a heater that atomizes the liquid. Some such electronic cigarettes include an atomizer assembly in which a coiled heater is wound around a wick that is fluidly connected to a tank (for example, see PTL 1).

CITATION LIST

Patent Literature

PTL 1: U.S. Pat. No. 8,528,569

SUMMARY OF INVENTION

Technical Problem

An object of the present disclosure is to provide a cartridge for an inhaler having a novel structure, and the inhaler.

Solution to Problem

According to a first embodiment of the present disclosure, there is provided a cartridge for an inhaler including a heater unit configured to atomize a liquid to generate aerosol, wherein the heater unit includes a liquid holding member that has a first surface, and a second surface facing the first surface, a heater that contacts the first surface of the liquid holding member, and a support member that supports the second surface of the liquid holding member and is softer than the liquid holding member.

In one embodiment, the first surface of the liquid holding member has a convex shape. The support member has a first convex surface that supports the second surface of the liquid holding member.

In one embodiment, the support member further has a second convex surface facing the first convex surface, a first side portion, and a second side portion facing the first side portion. A space is formed by the second convex surface, an inner surface of the first side portion, and an inner surface of the second side portion.

In one embodiment, the cartridge further includes a base member that holds at least a part of the support member and is harder than the support member.

In one embodiment, the base member has a base and holds the support member so that a space exists between the base and the support member.

In one embodiment, the base member has at least two first protrusions, and the at least two first protrusions contact an apex of the second convex surface.

In one embodiment, each of the at least two first protrusions also contacts the inner surface of the first side portion or the inner surface of the second side portion.

In one embodiment, the heater and the at least two first protrusions are arranged not to overlap each other when the heater unit is viewed from the base member side.

In one embodiment, the base member has at least two second protrusions, and the at least two second protrusions contact a portion below an apex of the second convex surface.

In one embodiment, the heater is a linear heater.

In one embodiment, the cartridge further includes a tank unit that is to be engaged with the heater unit. The tank unit is provided with a tank body that has a tank for storing the liquid, an aerosol flow path which is separated from the tank and through which the aerosol passes, and a chamber communicating with the aerosol flow path. A part of the liquid holding member and the heater are exposed to inside of the chamber, and another part of the liquid holding member is exposed to the inside of the tank.

According to a second embodiment of the present disclosure, there is provided a cartridge for an inhaler including a heater unit configured to atomize a liquid to generate aerosol, the cartridge having a proximal end which is located close to a mouth of a user when the user is using an inhaler, and a distal end on an opposite side from the proximal end, wherein the heater unit includes a heater that has a first end part and a second end part, a first electrode to which the first end part is to be connected, and a second electrode to which the second end part is to be connected, wherein at least one electrode of the first electrode and the second electrode has a first portion to which one of the first end part and the second end part is to be connected, and a second portion extending from an end on the proximal end side of the first portion in a direction toward the proximal end.

In one embodiment, the first electrode and the second electrode have substantially the same shape.

In one embodiment, in a boundary between the first portion and the second portion, a width of the first portion is wider than the width of the second portion.

In one embodiment, an end of the heater is connected to a portion which does not contact the second portion in an end on the proximal end side of the first portion.

In one embodiment, the first portion and the second portion form an L shape.

In one embodiment, the heater has a convex shape, and at least part of the second portion of each of the first electrode and the second electrode is located on the proximal end side from an uppermost top of the convex shape.

In one embodiment, the heater is a linear heater.

In one embodiment, the cartridge further includes a tank unit that is to be engaged with the heater unit. The tank unit is provided with a tank body that has a tank for storing the liquid, an aerosol flow path through which the aerosol passes, a chamber communicating with the aerosol flow path, and a first air inlet port and a second air inlet port that communicate with the chamber.

In one embodiment, at least a part of at least one air inlet port of the first air inlet port and the second air inlet port is located on the distal end side from an uppermost top of the second portion of an electrode closest to the air inlet port.

In one embodiment, at least a part of at least one air inlet port of the first air inlet port and the second air inlet port is located on the second portion side from an end of a portion which does not contact the second portion in an end on the proximal end side of the first portion of an electrode closest to the air inlet port.

In one embodiment, at least one air inlet port of the first air inlet port and the second air inlet port has a substantially circle shape.

In one embodiment, a center of the substantial circle of at least one air inlet port of the first air inlet port and the second air inlet port is located on the distal end side from an uppermost top of the second portion of an electrode closest to the air inlet port.

In one embodiment, a center of the substantial circle of at least one air inlet port of the first air inlet port and the second air inlet port is located on the second portion side from an end of a portion which does not contact the second portion in an end on the proximal end side of the first portion of an electrode closest to the air inlet port.

In one embodiment, when the first portion and the second portion of at least one electrode of the first electrode and the second electrode form an L shape, a predetermined percentage or more of an area of an air inlet port closest to the electrode out of the first air inlet port and the second air inlet port is located in a notch formed by the L-shape of the electrode.

In one embodiment, at least one air inlet port of the first air inlet port and the second air inlet port and the first portion and second portion of an electrode closest to the air inlet port are arranged not to overlap each other.

According to a third embodiment of the present disclosure, there is provided a cartridge for an inhaler, having a proximal end which is located close to a mouth of a user when the user is using an inhaler, and a distal end on an opposite side from the proximal end, the cartridge including a tank body and a cover member that are fitted with each other to define a tank for storing a liquid and an aerosol flow path extending in a direction connecting the proximal end and the distal end, and a flexible cap member that is arranged between the tank body and the cover member and has a hole communicating with the aerosol flow path.

In one embodiment, the tank body includes an inner side wall forming the aerosol flow path. The tank is separated from the aerosol flow path by the cap member and the inner side wall.

In one embodiment, the cap member includes a flat-plate portion having the hole, and a side wall portion extending from an edge of the flat-plate portion in a direction toward the distal end and surrounding an end on the proximal end side of the inner side wall.

In one embodiment, a shape of the flat-plate portion includes a first side and a second side that are substantially parallel to each other, a third side that connects one end of the first side and one end of the second side, and a fourth side that connects the other end of the first side and the other end of the second side. A distance between the first side and the second side is shorter than a maximum distance between the third side and the fourth side.

In one embodiment, the first side and the second side are substantially linear, and the third side and the fourth side are substantially arcuate.

In one embodiment, a shape formed by inside of a side wall of the tank body when viewed from the proximal end side includes a fifth side that is substantially parallel to the first side, a sixth side that is substantially parallel to the second side, a seventh side that connects one end of the fifth side and one end of the sixth side, and an eighth side that connects the other end of the fifth side and the other end of the sixth side. A distance between the fifth side and the sixth side is shorter than a maximum distance between the seventh side and the eighth side.

In one embodiment, the hole is a substantial circle.

In one embodiment, the cartridge includes a tank unit including the tank body, the cover member, and the cap member, and a heater unit that is to be engaged with the tank unit and is configured to atomize the liquid to generate the aerosol.

DESCRIPTION OF EMBODIMENTS

Figure 1:
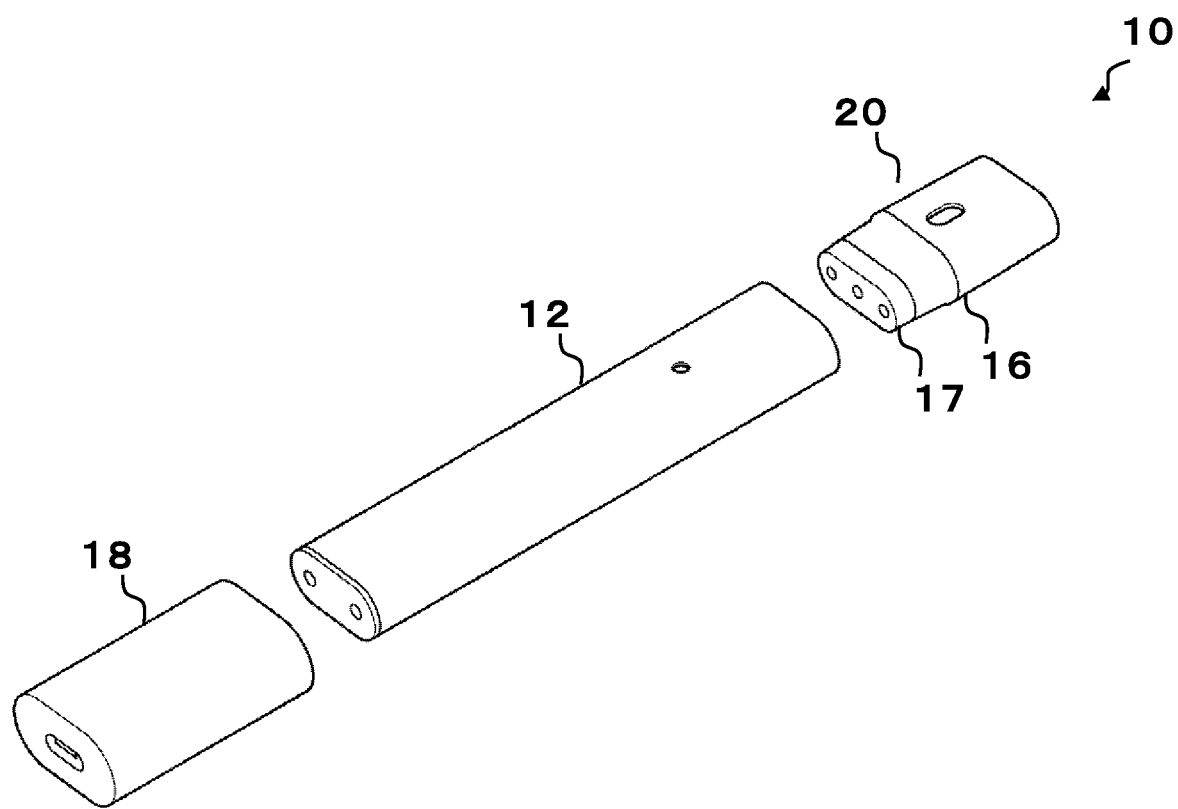
FIG. 1 is an overall perspective view of an inhaler according to one embodiment of the present disclosure.

Hereinafter, embodiments of the present disclosure will be described with reference to the drawings. In the drawings, the same or equivalent constituent elements are designated with the same reference numerals, and a repetitive description will be omitted.

FIG. 1 is an overall perspective view of an inhaler according to an embodiment of the present disclosure. As illustrated in FIG. 1, an inhaler 10 includes a cartridge 20 (corresponding to an example of a cartridge for an inhaler), and a battery unit 12. The cartridge 20 atomizes a liquid containing an aerosol-forming material such as glycerin or propylene glycol, and generates aerosol. The aerosol-forming material may contain, for example, a flavor source such as nicotine. The battery unit 12 supplies electric power to the cartridge 20. The cartridge 20 is formed by engaging a tank unit 16 with a heater unit 17. A cover member to be described later included in the tank unit 16 may have a function as a mouthpiece, or may be configured to guide the aerosol generated in the heater unit 17 to a mouth of a user. After the inhaler 10 is used over a predetermined period of time, the cartridge 20 can be changed.

As illustrated in FIG. 1, the inhaler 10 may be configured so that a charging unit 18 can be coupled to an end of the battery unit 12. The charging unit 18 may be, for example, a USB charger. In this case, the battery unit 12 can be connected to each USB port of various devices via the charging unit 18, and a power source (not illustrated) in the battery unit 12 can be charged by power supply from the USB port.

Figure 2:
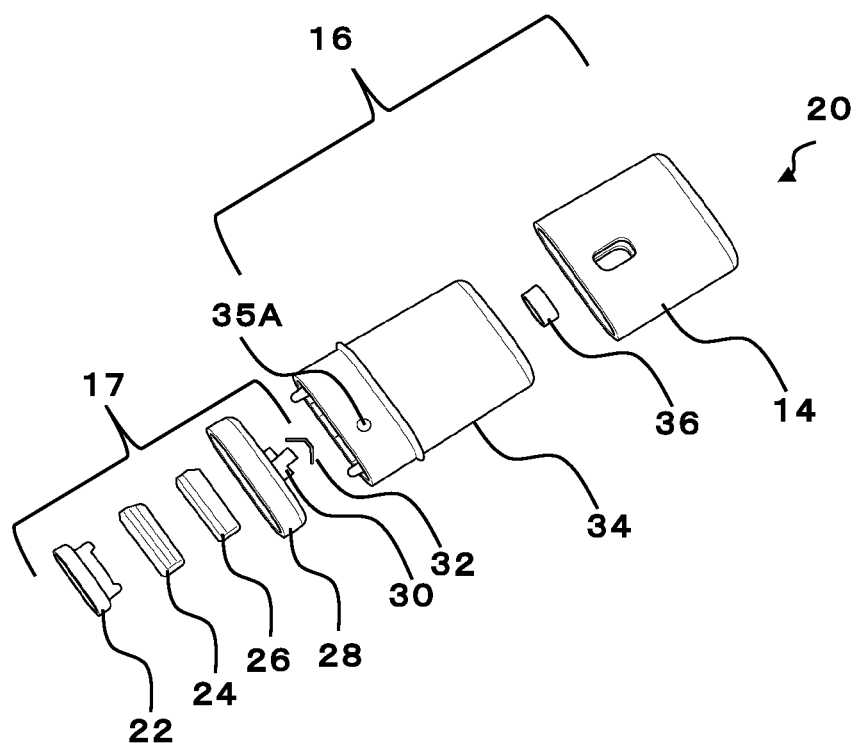
FIG. 2 is an exploded perspective view of a cartridge 20 according to one embodiment of the present disclosure.

Hereinafter, the cartridge 20 illustrated in FIG. 1 will be described in detail. FIG. 2 is an exploded perspective view of the cartridge 20 according to one embodiment of the present disclosure.

The cartridge 20 is formed by engaging the tank unit 16 with the heater unit 17. The tank unit 16 may include a cover member 14, a tank body 34, and a cap member 36. The tank body 34 has a plurality of air inlet ports (hereinafter, collectively referred to as "air inlet ports 35") including a first air inlet port 35A for communicating with a chamber and an aerosol flow path to be described later. The heater unit 17 may include a base member 22, a support member 24, a liquid holding member 26, an electrode holding member 28, an electrode 30, and a heater 32. The electrode 30 may include a pair of electrodes 30A and 30B as described later.

Here, the outline of steps of manufacturing the cartridge 20 will be described. Firstly, in a first step, the electrodes 30A and 30B and the electrode holding member 28 are integrally formed. In a second step, the heater 32 is soldered between the electrode 30A and the electrode 30B. On the other hand, in a third step, the base member 22, the support member 24, and the liquid holding member 26 are combined. Next, in a fourth step, a structure made up of the base member 22, the support member 24 and the liquid holding member 26 is press-fitted to a structure made up of the electrode holding member 28, the electrodes 30A and 30B, and the heater 32, to thereby form the heater unit 17. Separately from the first to fourth steps, in a fifth step, the cap member 36 is press-fitted to the tank body 34. Next, in a sixth step, the tank body 34 to which the cap member 36 is press-fitted and the cover member 14 are engaged by welding. Next, in a seventh step, the liquid (containing the aerosol-forming material) is injected into a tank in the tank body 34, to thereby form the tank unit 16. Finally, in an eighth step, the heater unit 17 and the tank unit 16 are engaged by welding.

Figure 3A:
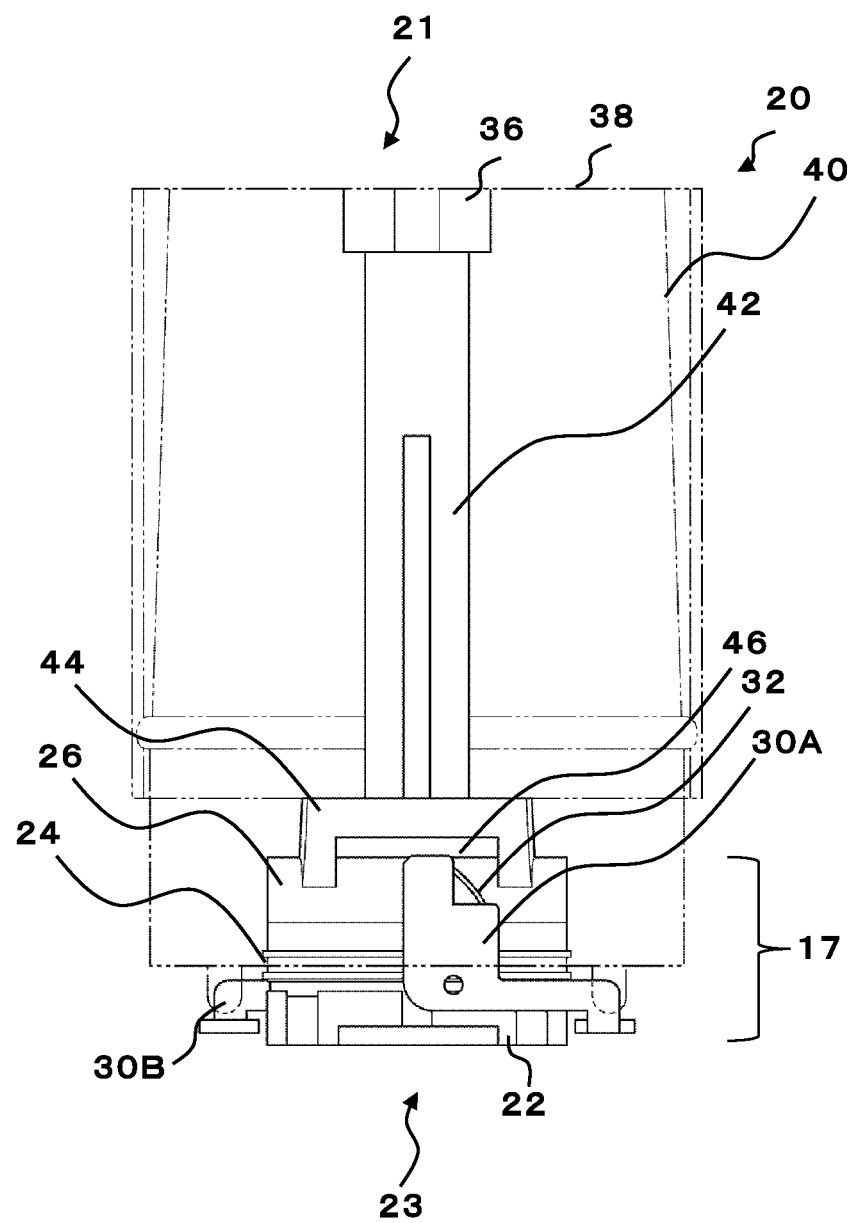
FIG. 3A is a transparent view of the cartridge with a cover member and an electrode holding member removed, according to one embodiment of the present disclosure.
Figure 3B:
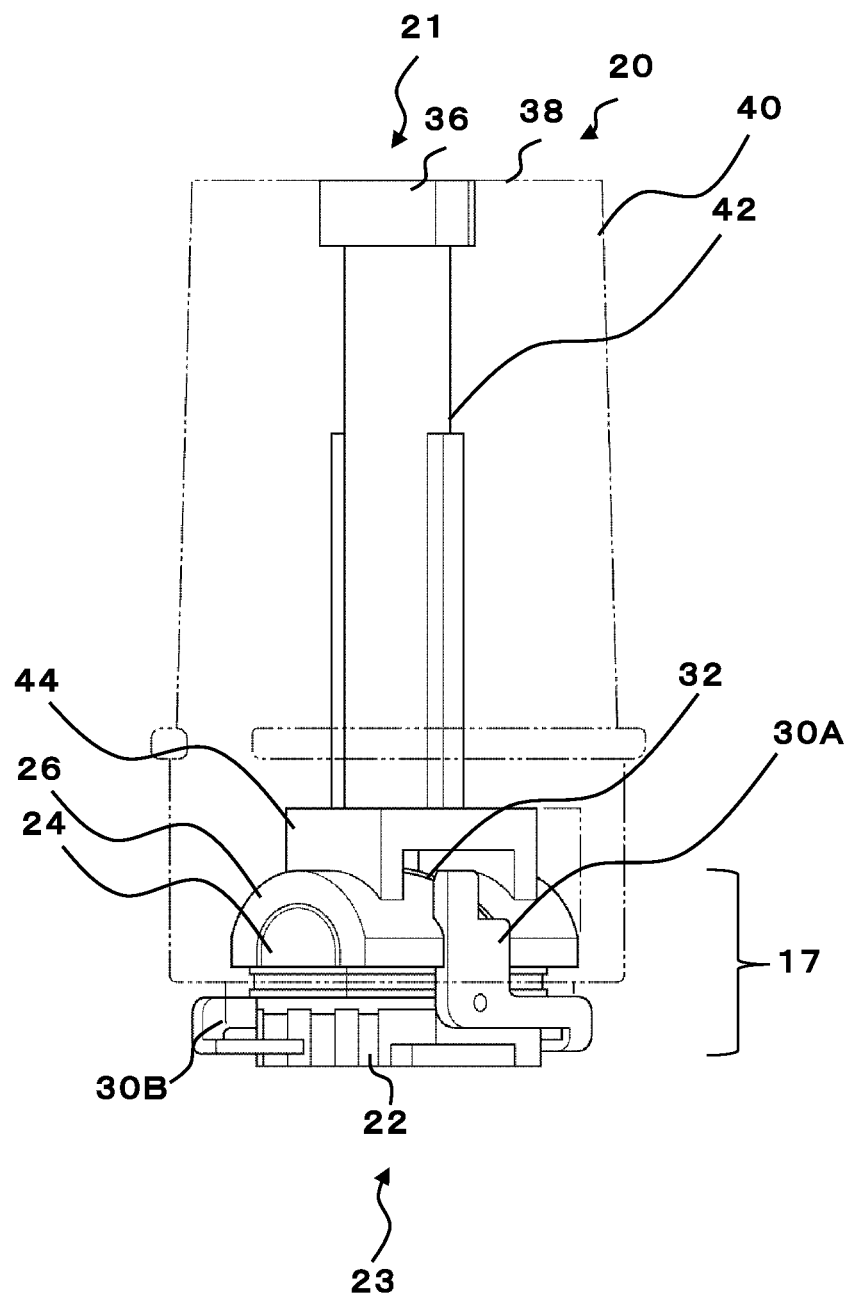
FIG. 3B is a perspective view of the cartridge illustrated in FIG. 3A in a position turned.
Figure 4:
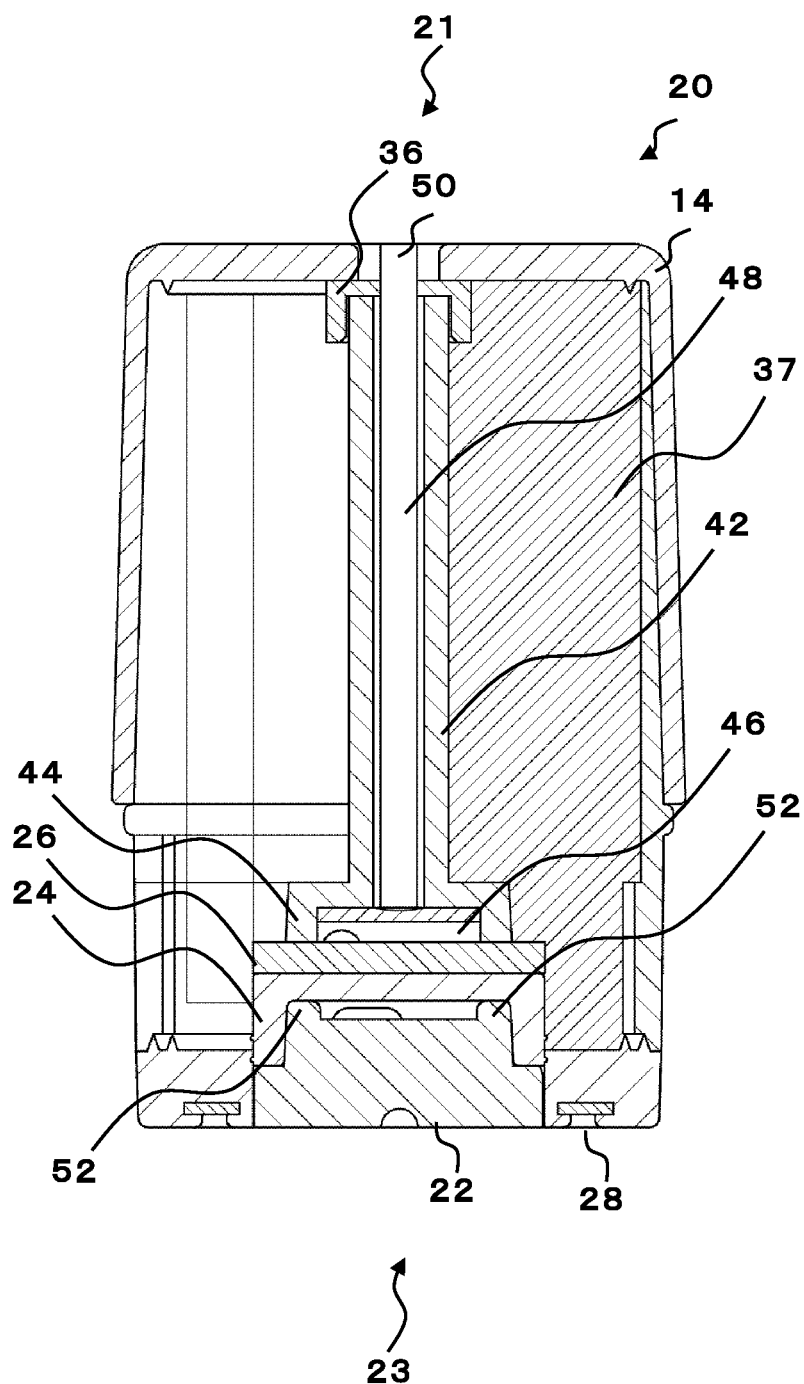
FIG. 4 is a cross-sectional view of the cartridge with the electrode and the heater removed, according to one embodiment of the present disclosure.

FIG. 3A is a transparent view of the cartridge 20 with the cover member 14 and the electrode holding member 28 removed according to the embodiment of the present disclosure. FIG. 3B is a perspective view of the cartridge 20 illustrated in FIG. 3A in a position turned about a direction connecting a proximal end 21 and a distal end 23 as an axis. FIG. 4 is a cross-sectional view of the cartridge 20 with the electrode 30 and the heater 32 removed.

As illustrated in FIGS. 3A, 3B, and 4, the cartridge 20 has the proximal end 21 and the distal end 23. The proximal end 21 is an end which is located close to the mouth of the user when the user is using the inhaler 10. The distal end 23 is an end on the opposite side from the proximal end 21 or an end which is located close to the battery unit 12 and is away from the mouth of the user when the user is using the inhaler 10. In the present embodiment, for convenience, a direction connecting the proximal end 21 and the distal end 23 (an up-down direction in FIG. 3A) is referred to as a first direction, and a direction perpendicular to this direction is referred to as a second direction. The first direction can be also referred to as a longitudinal direction, and the second direction can be also referred to as a transverse direction. Note that in FIGS. 5, 7, 9, 10, and 11 to be described later, X, Y, and Z axes are shown. In these figures, the Z-axis direction coincides with the first direction, and the X-axis direction and the Y-axis direction coincide with the second direction.

The cartridge 20 (or the tank body 34 included in the cartridge 20) includes an upper wall 38, a side wall 40 having a substantially cylindrical shape, and an inner side wall 42 having a substantially cylindrical shape that is located inside the side wall 40. A space is defined in a gap between the side wall 40 and the inner side wall 42. This space serves as a tank 37 for storing the liquid containing the aerosol-forming material. A chamber-forming member 44 separating the tank 37 and the chamber 46 is provided on the distal end 23 side. An internal space of the inner side wall 42 forms an aerosol flow path 48 extending in the first direction. The chamber 46 communicates with the aerosol flow path 48. The cap member 36 is arranged on the proximal end 21 side. The cap member 36 separates the tank 37 and the aerosol flow path 48. The cap member 36 may also serve as a buffer for fitting the cover member 14 and the tank body 34 to form the tank unit 16.

The tank body 34 may be configured to include the tank 37 for storing the liquid, the aerosol flow path 48 which is separated from the tank 37 and through which the aerosol passes, and the chamber 46 communicating with the aerosol flow path 48.

The heater unit 17 is attached to the distal end 23 side of the cartridge 20. The heater unit 17 is not only configured to atomize the liquid to generate the aerosol, and but also has a function of a bottom wall that closes the distal end 23 side of the cartridge 20.

An aerosol discharge port 50 communicating with the aerosol flow path 48 via the cap member 36 is formed in a substantially center portion of the upper wall 38. The heater 32 is exposed to the inside of the chamber 46 over the entire length thereof. The air having flowed into the chamber 46 through the air inlet ports 35 reaches the inside of the mouth of the user through the aerosol flow path 48 and the aerosol discharge port 50. The aerosol generated in the chamber 46 passes through the aerosol flow path 48 while being mixed with the air, and reaches the inside of the mouth of the user from the aerosol discharge port 50. In this way, the aerosol generated in the entire length of the heater 32 can be efficiently transported to the aerosol discharge port 50. In other words, the aerosol can be prevented from accumulating in the chamber 46, and the attachment of the aerosol to a wall surface of the chamber 46 can be reduced.

Figure 5:
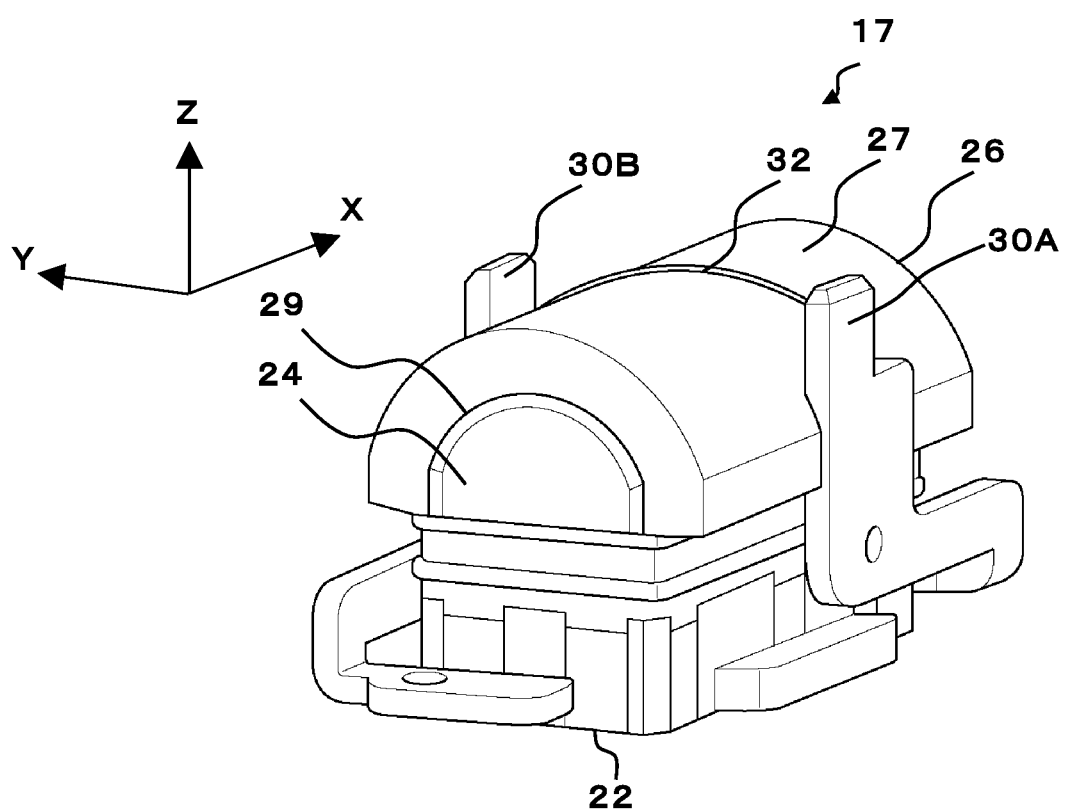
FIG. 5 is a perspective view of a heater unit with an electrode holding member removed, according to one embodiment of the present disclosure.

FIG. 5 is a perspective view of the heater unit 17 with the electrode holding member 28 removed. The heater unit 17 is configured to atomize the liquid to generate the aerosol. The heater unit 17 includes at least the support member 24, the liquid holding member 26, and the heater 32. The liquid holding member 26 may be formed of any porous member configured to transport the liquid containing the aerosol-forming material from the tank 37 to the heater 32. Since the liquid holding member 26 is in close contact with the heater 32, it is preferable that the liquid holding member 26 is formed of a fibrous member having flexibility such as cotton or a glass fiber. By way of example, the liquid holding member 26 may be formed by stacking two or more sheets of cotton. The liquid holding member 26 has a first surface 27 and a second surface 29 facing the first surface. The first surface 27 may have a convex shape. In the illustrated example, the first surface 27 is a ridge-shaped surface 27 protruding in the Z-axis direction. The convex shape of the ridge-shaped surface 27 illustrated in the figure may have a single apex in the Z-axis direction (i.e., a direction toward the proximal end when incorporated into the cartridge 20). The apex forms a straight line extending in the X-axis direction when viewed from the Y-axis direction. However, the convex shape of the first surface 27 is not limited thereto, and may have various a plurality of apexes in the Z-axis direction. The second surface 29 facing the first surface 27 is supported by the support member 24. The ridge-shaped surface 27 extends along the X-axis direction perpendicular to the Z-axis direction. In addition, the pair of electrodes 30A and 30B (hereinafter, collectively referred to as "electrodes 30") are arranged to be spaced from each other in the Y-axis direction perpendicular to both of the Z-axis direction which is a protruding direction of the ridge-shaped surface 27 and the X-axis direction which is an extending direction of the ridge-shaped surface 27. When the cartridge 20 is coupled to the battery unit 12, the electrodes 30 connect the heater 32 with a battery in the battery unit 12.

A center portion in the Y-axis direction of the first surface 27 (here, the ridge-shaped surface 27) of the liquid holding member 26 exists at a position different in the Z-axis direction from other portions in the Y-axis direction. Specifically, the center portion in the Y-axis direction of the liquid holding member 26 forms the apex of the ridge-shaped surface 27. In addition, the liquid holding member 26 is formed by deforming a disc-shaped or flat-plate-shaped porous member into a ridge shape. In the flat-plate-shaped porous member, the surface (the ridge-shaped surface 27) to be contacted by the heater 32 has a pair of long sides and a pair of short sides. When this flat-plate-shaped porous member is formed into a ridge shape, the liquid holding member 26 is deformed into a substantially U shape when viewed from the X-axis direction, as illustrated in FIG. 5.

The heater 32 has an element which is connected to the electrodes 30 to extend in a direction intersecting the protruding direction (Z-axis direction) of the ridge-shaped surface 27, and is arranged to intersect the apex of the ridge-shaped surface 27. The heater 32 is configured so that at least a portion thereof contacts the ridge-shaped surface 27 of the liquid holding member 26. Specifically, a predetermined-length portion of the heater 32 is arranged along the ridge-shaped surface 27 of the liquid holding member 26. It is preferable that the heater 32 contacts the ridge-shaped surface 27 of the liquid holding member 26 over substantially the entire length of the heater 32. In this case, the connection portion (for example, a welded portion) between each electrode 30 and the heater 32 may contact the ridge-shaped surface 27 of the liquid holding member 26. This enables the heater 32 to contact the ridge-shaped surface 27 over the entire length of the heater 32. In addition, a distance in the Y-axis direction between connection portions between the electrodes 30 and the heater 32 is shorter than a length of the heater 32 between the connection portions. That is, the heater 32 is arranged to deflect between the electrodes 30.

In one embodiment, a position of one end of the heater 32 connected to the first electrode 30A and a position of the other end of the heater 32 connected to the second electrode 30B may be misaligned with each other in the X-axis direction. That is, the heater 32 may be formed to extend not parallel to the Y-axis direction but obliquely with respect to the Y-axis direction.

In the cartridge 20 of the present embodiment, the ridge-shaped surface 27 protrudes toward the aerosol discharge port 50 side. Thus, an evaporation direction of the aerosol when the heater 32 is energized coincides with an air flow when inhaling, whereby the frequency of contact between the generated aerosol and the wall surface forming the flow path can be reduced to reduce condensation of the aerosol on the wall surface of the chamber 46.

As illustrated in FIG. 5, it is preferable that the heater 32 is arranged to be pressed against the ridge-shaped surface 27 of the liquid holding member 26. It is preferable that the liquid holding member 26 is made of a material (material having the flexibility) which can be deformed by pressing the heater 32 against the liquid holding member 26. The heater 32 may be, for example, a single or a plurality of linear heaters, or may be formed into any shape such as a mesh shape or a plate shape. When the heater 32 is a single linear heater as in the present embodiment, for example, the thermal capacity thereof can be smaller than that of the mesh-shaped or plate-shaped heater, whereby the liquid can be efficiently atomized.

As illustrated in FIG. 5, the support member 24 supports the second surface 29 facing the ridge-shaped surface 27 of the liquid holding member 26. More specifically, the support member 24 may be configured to support a position of the second surface 29 facing a position of the ridge-shaped surface 27 contacted by the heater 32. In this way, the ridge shape of the liquid holding member 26 can be maintained even when the heater 32 is arranged to be pressed against the ridge-shaped surface 27 of the liquid holding member 26 so that the liquid holding member 26 receives a predetermined force from the heater 32. In addition, the second surface 29 of the liquid holding member 26 contacts the support member 24, and nothing is provided between the second surface 29 and the support member 24. That is, the heater 32 is provided only on the ridge-shaped surface 27. Accordingly, when the heater 32 atomizes the liquid held in the liquid holding member 26, the aerosol becomes unlikely to be generated from the second surface 29, and is preferentially generated from the ridge-shaped surface 27. The support member 24 is formed as a member separate from the base member 22. The length (width) in the Y-axis direction and the length in the X-axis direction of the support member 24 are arbitrary, and the support member 24 is designed to form a desired ridge-shaped surface 27.

If the contact between the heater 32 and the liquid holding member 26 is too thin, the heater 32 is deformed at the time of heat generation, causing separation from the liquid holding member 26, which may make it difficult to efficiently generate the aerosol. If the contact between the heater 32 and the liquid holding member 26 is too thick, the heater 32 is excessively embedded in the liquid holding member 26, which may cause the bumping of the liquid held in the liquid holding member 26. In the present embodiment, the support member 24 is formed to be softer than the liquid holding member 26. The term "softness" means the ease of deformation of each member when the heater 32 is in contact with the liquid holding member 26. That is, when the heater 32 is in contact with the liquid holding member 26 in a state in which the support member 24 and the liquid holding member 26 are stacked, the support member 24 is deformed before the liquid holding member 26 is deformed. By way of example, when the liquid holding member 26 is formed of cotton, the support member 24 may contain silicone rubber. When the heater 32 is pressed against the liquid holding member 26, the support member 24 is deformed before the liquid holding member 26 is deformed, which can reduce the embedding of the heater 32 in the liquid holding member 26 and can fix the heater 32 so that the heater 32 is not detached from the liquid holding member 26 in use.

The base member 22 may be configured to be harder than the support member 24. However, it is preferable that the base member 22 is made of a resin material such as PET or PP. In addition, the base member 22 may be configured to be harder than the liquid holding member 26. In this case, among the base member 22, the support member 24, and the liquid holding member 26, the support member 24 is the softest, the liquid holding member 26 is the next softest, and the base member 22 is the hardest.

For example, as the softness (hardness), the hardness measured by a durometer or the like can be used. For example, the hardness of the support member 24 is preferably 10 to 30, and the hardness of the base member 22 is preferably 80 or more.

When the cartridge 20 is formed by engaging the tank unit 16 with the heater unit 17, the liquid holding member 26 is compressed by the base member 22, the electrode holding member 28, the chamber-forming member 44, and the like. The liquid holding member 26 is sandwiched between the chamber-forming member 44 and the support member 24. Then, a part of the liquid holding member 26 and the heater 32 are exposed to the inside of the chamber 46, and another part of the liquid holding member 26 is exposed to the inside of the tank 37. The liquid in the tank 37 is supplied from the part of the liquid holding member 26 which is exposed to the inside of the tank 37 to the part of the liquid holding member 26 which is exposed to the inside of the chamber 46 utilizing capillary force.

The part of the liquid holding member 26 which is exposed to the inside of the tank 37 may be impregnated and spread in the liquid stored in the tank 37. The part of the liquid holding member 26 which is exposed to the inside of the chamber 46 may absorb the liquid supplied from the tank 37 and expand. Accordingly, it should be noted that the liquid holding member 26 in the completed cartridge 20 may have a shape deformed more than the above-described basic shape.

Figure 6:
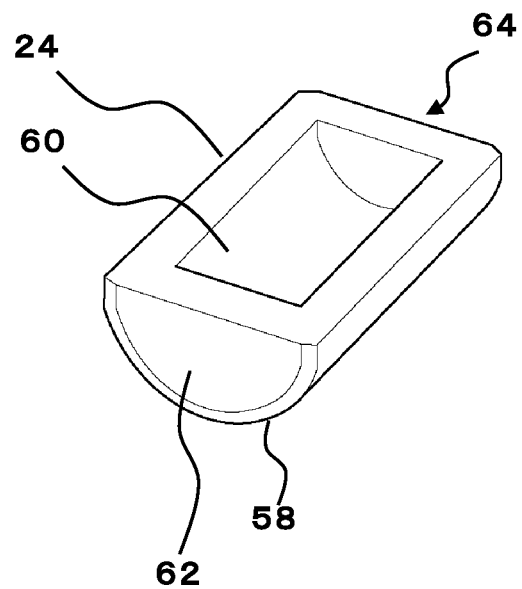
FIG. 6 is a perspective view of a support member according to one embodiment of the present disclosure.

FIG. 6 is a perspective view of an exemplary support member 24. It should be noted that in FIG. 6, the support member 24 is illustrated upside down with respect to that illustrated in FIG. 5 to illustrate the internal structure of the support member 24. The support member 24 has a first convex surface 58 that supports the second surface 29 of the liquid holding member 26. The support member 24 also has a second convex surface 60 facing the first convex surface 58, a first side portion 62, and a second side portion 64 facing the first side portion 62. As will be understood from FIG. 6, a space is formed by the second convex surface 60, an inner surface of the first side portion 62, and an inner surface of the second side portion 64.

The first convex surface 58 of the support member 24 may have a single apex in a direction (Z-axis direction) toward the proximal end, when incorporated into the cartridge 20. However, the shape of the first convex surface 58 is not limited thereto, and may have various a plurality of apexes in the Z-axis direction. The second convex surface 60 may have a similar shape to the first convex surface 58 or a different shape from the first convex surface 58.

As illustrated in FIG. 6, the first side portion 62 and the second side portion 64 may be arranged to be coupled to the ends of the first convex surface 58 in the X-axis direction, respectively, or may be flat plates having a shape (substantially semicircular shape in an example in FIG. 6) conforming to the shape of the end of the first convex surface 58.

The base member 22 holds at least a part of the support member 24. The base member 22 may have a base 51 and hold the support member 24 so that a space exists between the base 51 and the support member 24. The base member 22 may have one or a plurality of protrusions. For example, as illustrated in FIG. 4, the base member 22 may have at least two first protrusions 52. The at least two first protrusions 52 may contact the apex of the second convex surface 60. In this case, the protrusions 52 of the base member 22 mainly contact an inner surface of the support member 24, whereby a space is generated between the base member 22 and the support member 24. With such a configuration, the degree of freedom of deformation of the support member 24 is increased when the heater 32 is pressed against the liquid holding member 26.

Furthermore, each of the at least two first protrusions 52 of the base member 22 may contact the inner surface of the first side portion 62 of the support member 24 or the inner surface of the second side portion 64 of the support member 24. In this case, the heater 32, the liquid holding member 26, the support member 24, the space generated by existence of the protrusions 52, and the base member 22 are located in the direction from the chamber 46 toward the distal end 23.

The base member 22 may have at least two second protrusions 53. The at least two second protrusions 53 may contact a portion below the apex of the second convex surface 60 of the support member 24. Two of the at least two first protrusions 52 may be arranged to face each other along a particular direction (for example, the X-axis direction). Two of the at least two second protrusions 53 may be arranged to face each other along a direction (for example, the Y-axis direction) different from the above-described direction.

Figure 7:
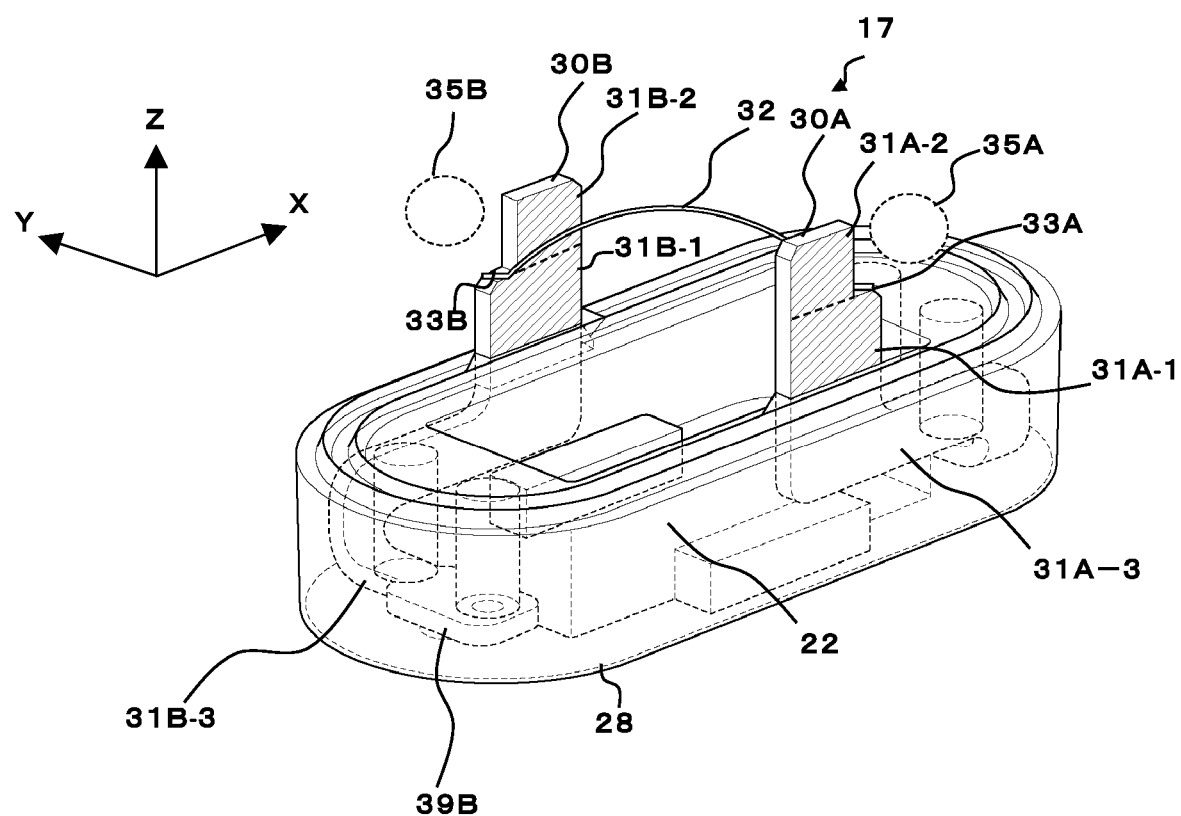
FIG. 7 is a perspective view of a heater unit with the support member and the liquid holding member removed, according to one embodiment of the present disclosure.

FIG. 7 is a perspective view of the heater unit 17 with the support member 24 and the liquid holding member 26 removed. The heater 32 has ends 33 including a first end part 33A and a second end part 33B that are to be connected to the electrodes 30 including the first electrode 30A and the second electrode 30B, respectively. The heater 32 may a linear heater, or may be configured to include one or a plurality of linear heater portions. The heater 32 and the at least two first protrusions 52 of the base member 22 may be arranged not to overlap each other when the heater unit 17 is viewed from the base member 22 side. Alternatively, the heater 32 may be arranged to intersect a line connecting the at least two first protrusions 52.

In an example in FIG. 7, the first end part 33A of the heater 32 is connected to the first electrode 30A, and the second end part 33B is connected to the second electrode 30B. The first electrode 30A and the second electrode 30B may have substantially the same shape. The first electrode 30A and the second electrode 30B may be arranged to be substantially symmetrical with each other about the X-axis direction. Furthermore, the first electrode 30A and the second electrode 30B may be arranged to be substantially symmetrical with each other about the Y-axis direction. Accordingly, in one example, as illustrated in FIG. 7, the heater 32 may be arranged not parallel to the Y-axis direction but obliquely with respect to the Y-axis direction. According to this configuration, the length of the heater 32 is increased as compared with a case where the pair of ends 33 are connected to the pair of electrodes 30 at the same positions in the X-axis direction. Accordingly, a contact area between the heater 32 and the ridge-shaped surface 27 of the liquid holding member 26 can be increased. Note that in another example, the pair of electrodes 30 may be arranged at the same positions in the X-axis direction. In this case, the pair of ends 33 may be also connected to the pair of electrodes 30 at the same positions in the X-axis direction. In addition, it will be understood that the electrode 30 and the end 33A may be arranged at various positions.

The ends 33 are located on the distal end 23 side of the apex of the ridge-shaped surface 27 of the liquid holding member 26. That is, the heater 32 curves along the ridge-shaped surface 27 of the liquid holding member 26 to contact the ridge-shaped surface 27. This can sufficiently ensure the contact area between the heater 32 and the ridge-shaped surface 27 of the liquid holding member 26.

As illustrated in FIGS. 4 and 7, the electrode holding member 28 forms, together with the base member 22, a bottom wall forming the distal end 23 of the cartridge 20. When the cartridge 20 is coupled to the battery unit 12 as illustrated in FIG. 1, portions of the electrodes 30 extending to the outside of the bottom wall are configured to be connected to a battery terminal (not illustrated) of the battery unit 12. This enables the battery unit 12 to supply the electric power to the heater 32 through the electrodes 30.

In one embodiment, at least one electrode of the first electrode 30A and the second electrode 30B has a first portion to which one of the first end part 33A and the second end part 33B is to be connected and a second portion extending from an end on the proximal end 21 side of the first portion in the direction toward the proximal end 21. For example, as illustrated in FIG. 7, the first electrode 30A may have a first portion 31A-1 to which the first end part 33A is to be connected and a second portion 31A-2 extending from the end on the proximal end 21 side of the first portion 31A-1 in the direction toward the proximal end 21. Instead of the above-described configuration or in addition to the above-described configuration, the second electrode 30B may have a first portion 31B-1 to which the second end part 33B is to be connected and a second portion 31B-2 extending from an end on the proximal end 21 side of the first portion 31B-1 in the direction toward the proximal end 21.

In FIG. 7, a dotted line drawn between the first portion 31A-1 and the second portion 31A-2 of the first electrode 30A indicates a boundary therebetween. A dotted line drawn between the first portion 31B-1 and the second portion 31B-2 of the second electrode 30B indicates a boundary therebetween. In one example, as illustrated in the figure, in the boundary between the first portion and the second portion, the width of the first portion is wider than the width of the second portion. In an example in FIG. 7, the first portion and the second portion each have a rectangular shape. However, it will be understood that the shapes of the first portion and the second portion are not limited to the rectangular shape, and may have various shapes such as a shape tapering toward the proximal end 21.

As illustrated in FIG. 7, the first end part 33A of the heater 32 may be connected to a portion which does not contact the second portion 31A-2 in the end on the proximal end 21 side of the first portion 31A-1. The second end part 33B of the heater 32 may be connected to a portion which does not contact the second portion 31B-2 in the end on the proximal end 21 side of the first portion 31B-1.

As indicated by hatched lines in FIG. 7, the first portion 31A-1 and the second portion 31A-2 of the first electrode 30A may form an L shape. Similarly, the first portion 31B-1 and the second portion 31B-2 of the second electrode 30B may form an L shape.

As illustrated in the figure, the second electrode 30B may include a third portion 31B-3 extending from the first portion 31B-1 in a direction toward the distal end 23, in addition to the first portion 31B-1 and the second portion 31B-2. In one example, the third portion 31B-3 extends from a lower end of the first portion 31B-1 along an inner side surface and an inner bottom surface of the electrode holding member 28. The third portion 31B-3 further includes an electrical contact 39B with the battery unit 12. Similarly, the first electrode 30A may also include a third portion 31A-3 extending from the first portion 31A-1 in a direction toward the distal end 23, in addition to the first portion 31A-1 and the second portion 31A-2. In one example, the third portion 31A-3 extends from a lower end of the first portion 31A-1 along an inner side surface and an inner bottom surface of the electrode holding member 28. Although not illustrated, the third portion 31A-3 further includes an electrical contact 39A with the battery unit 12.

FIG. 7 schematically illustrates the first air inlet port 35A illustrated in FIG. 2 and the second air inlet port 35B provided on the opposite side of the cartridge 20. At least one air inlet port of the first air inlet port 35A and the second air inlet port 35B may have a substantially circle shape or other various shapes. When the user inhales using the inhaler 10, air outside of the inhaler 10 flows into the chamber 46 through the first air inlet port 35A and the second air inlet port 35B, is mixed with the aerosol generated upon heat generation of the heater 32, and reaches the inside of the mouth of the user through the aerosol flow path 48 and the aerosol discharge port 50. According to the present embodiment, the electrodes 30 are arranged at positions so that air having flowed in through the air inlet ports 35 contacts the second portions of the electrodes 30. For example, the electrodes 30 may be configured so that their second portions are arranged along an air flow path. In this case, the air having flowed in through the air inlet ports 35 passes through while contacting the second portions, whereby the cooling effect of the electrodes 30 can be increased, which can provide an efficient heat dissipation function. That is, in the present embodiment, the second portion is a part of the electrode 30 and can also serve as a heat dissipation portion that effectively releases heat.

FIGS. 8A to 8E each illustrate an arrangement relationship between the first and second portions of the electrode and the air inlet port. FIGS. 8A to 8E each illustrate the arrangement relationship between the first electrode 30A and the first air inlet port 35A which is an air inlet port located closest to the first electrode 30A. However, it will be understood by those skilled in the art that the second electrode 30B and the second air inlet port 35B which is an air inlet port located closest to the second electrode 30B may be arranged in the same manner.

Figure 8A:
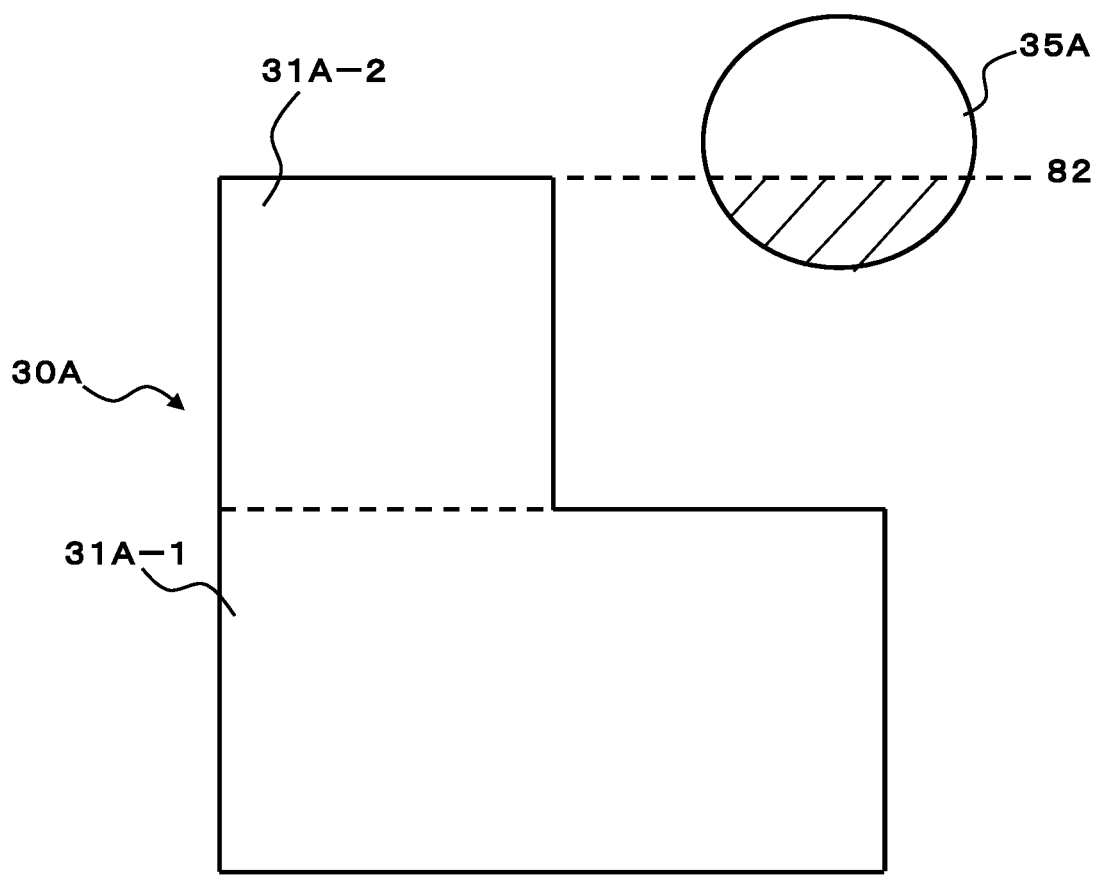
FIG. 8A illustrates an example of an arrangement relationship between first and second portions of the electrode and an air inlet port.

In one example, at least a part of at least one air inlet port of the first air inlet port 35A and the second air inlet port 35B may be located on the distal end side from the uppermost top of the second portion of the electrode closest to the air inlet port. FIG. 8A illustrates an example of such a structure. In FIG. 8A, a part (indicated by the hatched lines) of the first air inlet port 35A is located on the distal end 23 side from the uppermost top (indicated by a dotted line 82) of the second portion 31A-2 of the electrode (first electrode 30A) closest to the first air inlet port 35A.

Figure 8B:
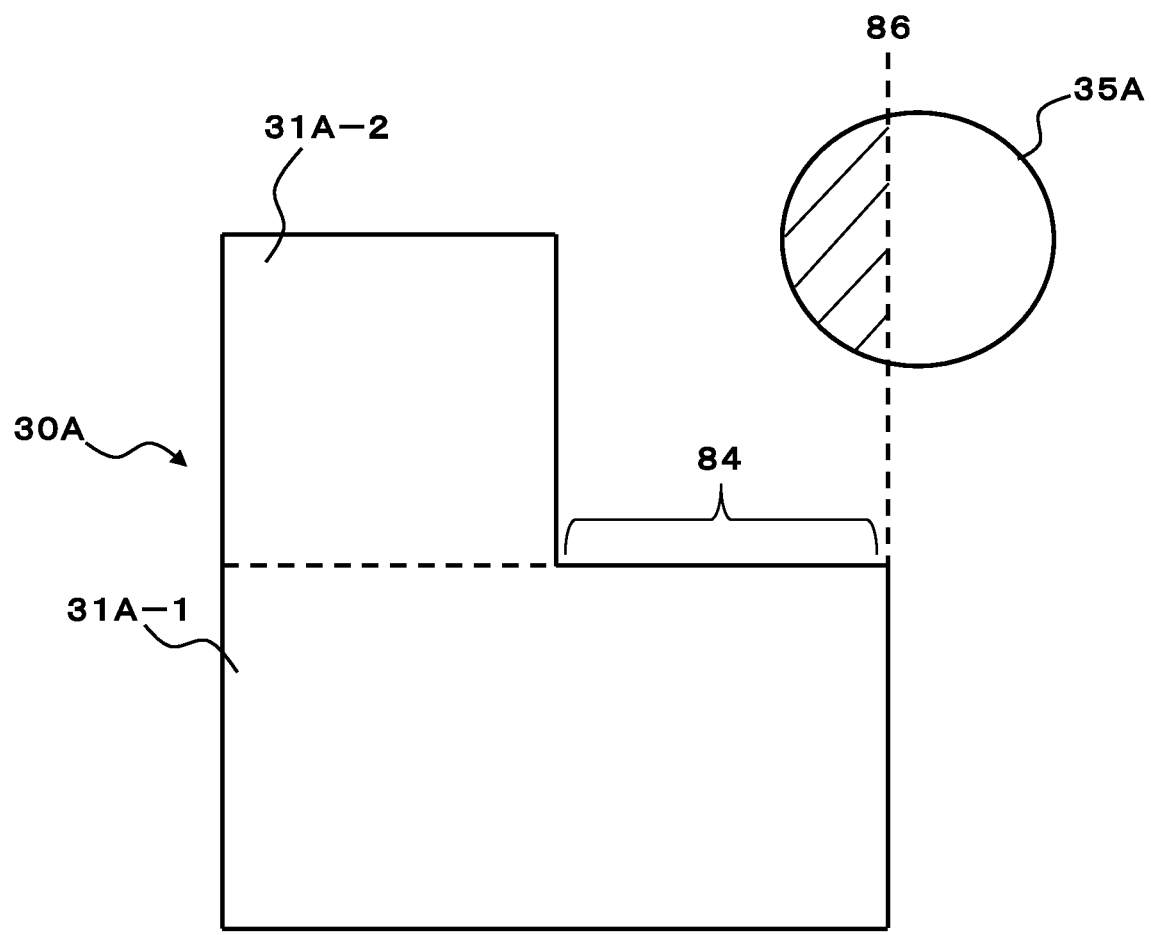
FIG. 8B illustrates an example of an arrangement relationship between the first and second portions of the electrode and the air inlet port.

In one example, at least a part of at least one air inlet port of the first air inlet port 35A and the second air inlet port 35B may be located on the second portion side from an end of a portion which does not contact the second portion in the end on the proximal end side of the first portion of the electrode closest to the air inlet port. FIG. 8B illustrates an example of such a structure. In FIG. 8B, a part (indicated by the hatched lines) of the first air inlet port 35A is located on the second portion side from an end (indicated by a dotted line 86) of a portion 84 which does not contact the second portion in the end on the proximal end 21 side of the first portion 31A-1 of the electrode (first electrode 30A) closest to the first air inlet port 35A.

Figure 8C:
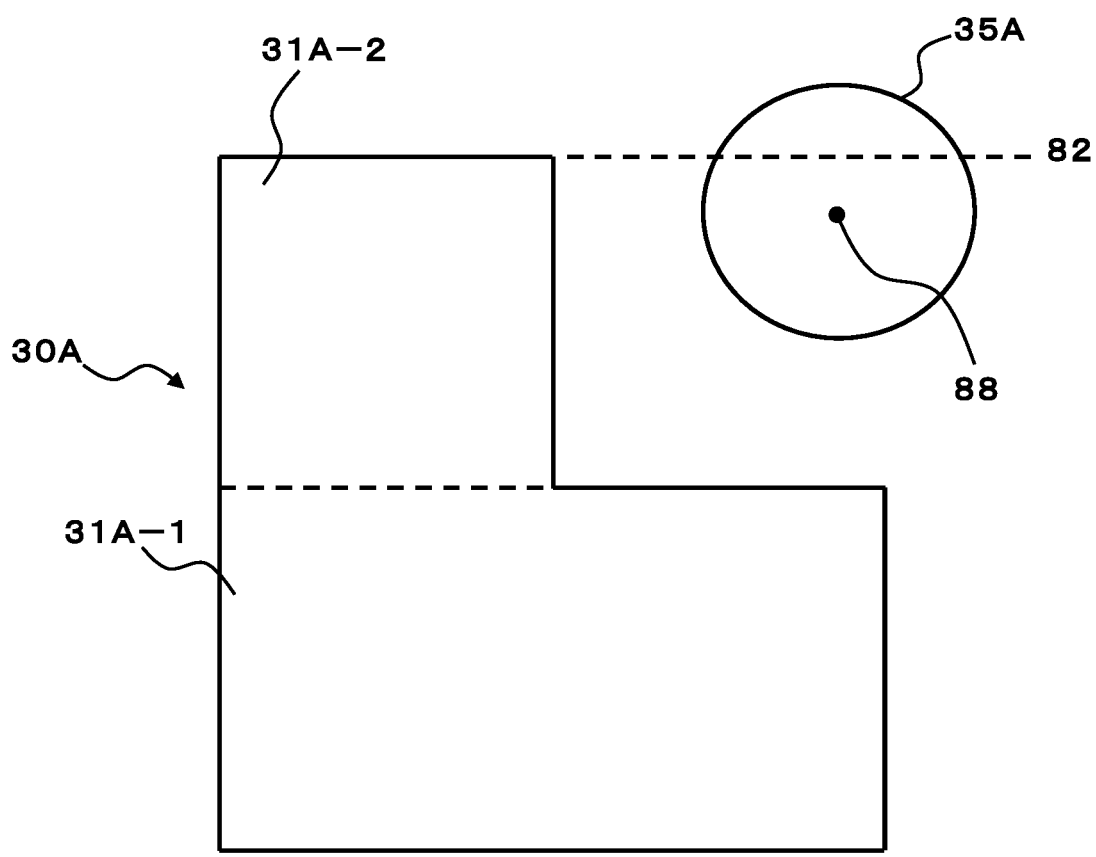
FIG. 8C illustrates an example of an arrangement relationship between the first and second portions of the electrode and the air inlet port.

In one example, a center of a substantial circle of at least one air inlet port of the first air inlet port 35A and the second air inlet port 35B may be located on the distal end side from the uppermost top of the second portion of the electrode closest to the air inlet port. FIG. 8C illustrates an example of such a structure. In FIG. 8C, a center 88 of the first air inlet port 35A is located on the distal end 23 side from the uppermost top (indicated by a dotted line 82) of the second portion 31A-2 of the electrode (first electrode 30A) closest to the first air inlet port 35A.

Figure 8D:
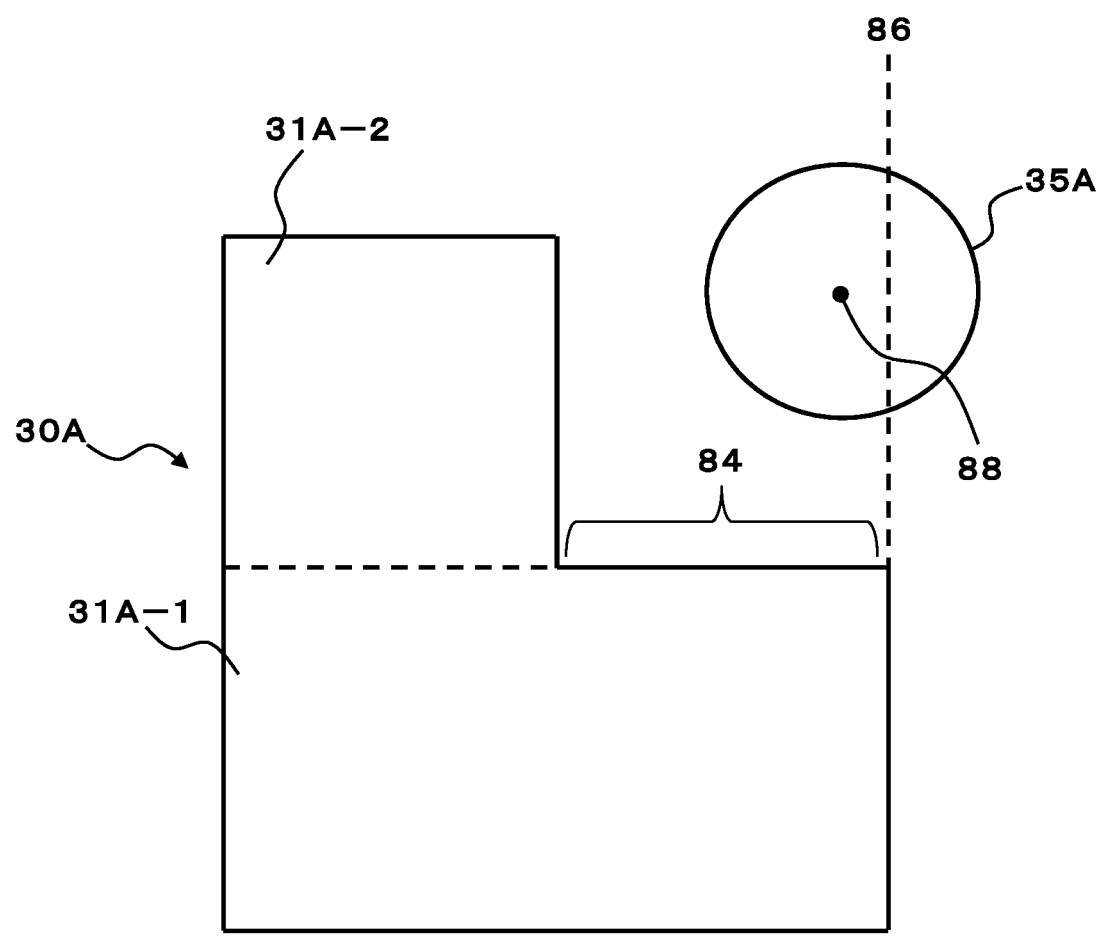
FIG. 8D illustrates an example of an arrangement relationship between the first and second portions of the electrode and the air inlet port.

In one example, a center of a substantial circle of at least one air inlet port of the first air inlet port 35A and the second air inlet port 35B may be located on the second portion side from an end of a portion which does not contact the second portion in the end on the proximal end side of the first portion of the electrode closest to the air inlet port. FIG. 8D illustrates an example of such a structure. In FIG. 8D, a center 88 of the first air inlet port 35A is located on the second portion side from an end (indicated by a dotted line 86) of a portion 84 which does not contact the second portion in the end on the proximal end 21 side of the first portion 31A-1 of the electrode (first electrode 30A) closest to the first air inlet port 35A.

Figure 8E:
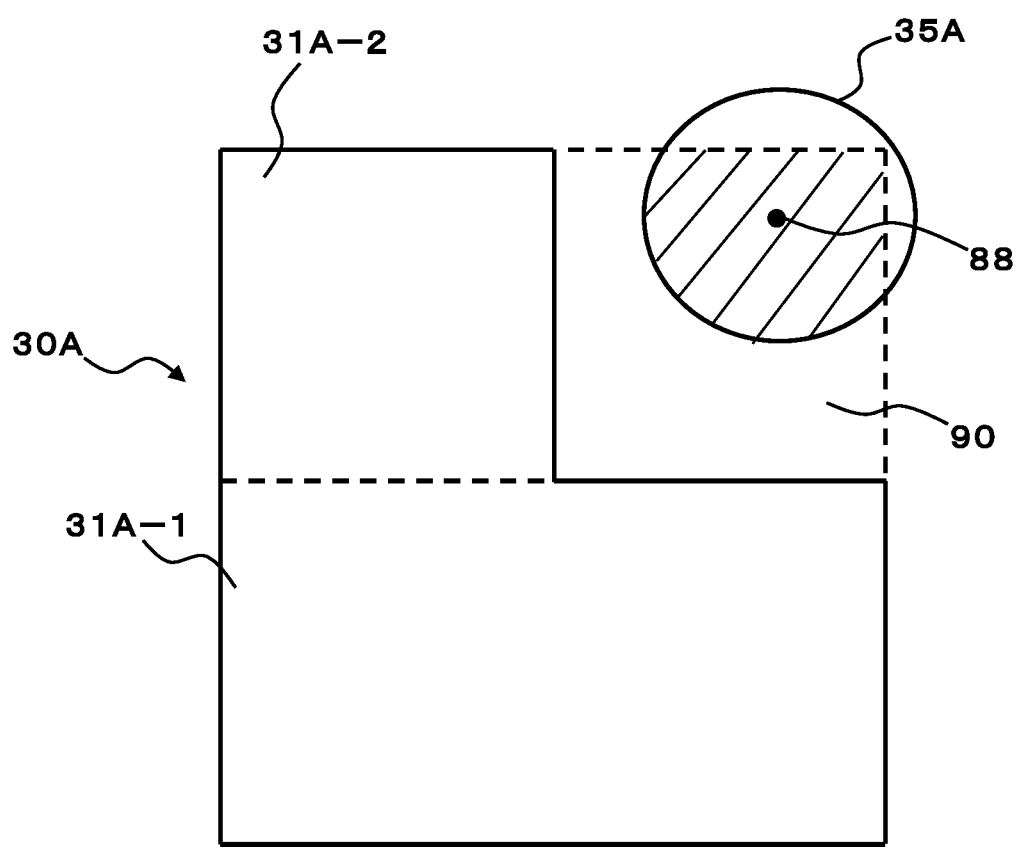
FIG. 8E illustrates an example of an arrangement relationship between the first and second portions of the electrode and the air inlet port.

In one example, when the first portion and the second portion of at least one electrode of the first electrode 30A and the second electrode 30B form an L shape, a predetermined percentage or more of an area of an air inlet port closest to the electrode out of the first air inlet port 35A and the second air inlet port 35B may be located in a notch formed by the L-shape of the electrode. FIG. 8E illustrates an example of such a structure. In FIG. 8E, the first portion 31A-1 and 31A-2 of the first electrode 30A form an L shape. A portion (indicated by hatched lines) greater than or equal to a predetermined percentage or more of an area of an air inlet port (first air inlet port 35A) closest to the first electrode 30A is located in a notch 90 formed by the L-shape of the first electrode 30A. The above-described predetermined percentage may be, for example, 50%, or other various percentages.

At least one air inlet port of the first air inlet port 35A and the second air inlet port 35B and the first portion and second portion of the electrode closest to the air inlet port may be arranged not to overlap each other when viewed in the Y-axis direction.

As illustrated in FIG. 7, the heater 32 may have a convex shape. At least a part of the second portion 31A-2 of the first electrode 30A may be located on the proximal end side from the uppermost top of the convex shape of the heater 32. In addition, at least a part of the second portion 31B-2 of the second electrode 30B may be located on the proximal end side from the uppermost top of the convex shape of the heater 32.

Note that the second portion of the electrode 30 can also serve as a guide when the heater unit 17 is combined with the other members to assemble the cartridge 20. The first electrode 30A and the second electrode 30B have the second portion 31A-2 and the second portion 31B-2, respectively, and these second portions are located above the heater 32 in the Z-axis direction, whereby the heater 32 can be prevented from being damaged due to unintended contact with the other members when the cartridge 20 is assembled.

The shape of a side surface of the cap member 36 will be understood from examples illustrated in FIGS. 3A, 3B, and 4. The tank body 34 and the cover member 14 are fitted with each other to define the tank 37 for storing the liquid and the aerosol flow path 48 extending in a direction connecting the proximal end 21 and the distal end 23. The cap member 36 is arranged between the tank body 34 and the cover member 14, and has a hole communicating with the aerosol flow path 48. The hole may form a substantial circle. The cap member 36 may be formed of a flexible material. As can be seen from FIG. 4, the cap member 36 is provided with a flat-plate portion having the hole, and a side wall portion extending from an edge of the flat-plate portion in the direction toward the distal end 23 and surrounding an end on the proximal end 21 side of the inner side wall 42. The tank body 34 includes the inner side wall 42 forming the aerosol flow path 48. As illustrated in FIG. 4, the cap member 36 may be engaged, in a U-shape, with a forward end of a tube structure formed by the inner side wall 42 forming the aerosol flow path 48. The tank 37 is separated from the aerosol flow path 48 by the cap member 36 and the inner side wall 42. Using such a cap member 36 can surely separate the tank 37 and the aerosol flow path 48.

Figure 9:
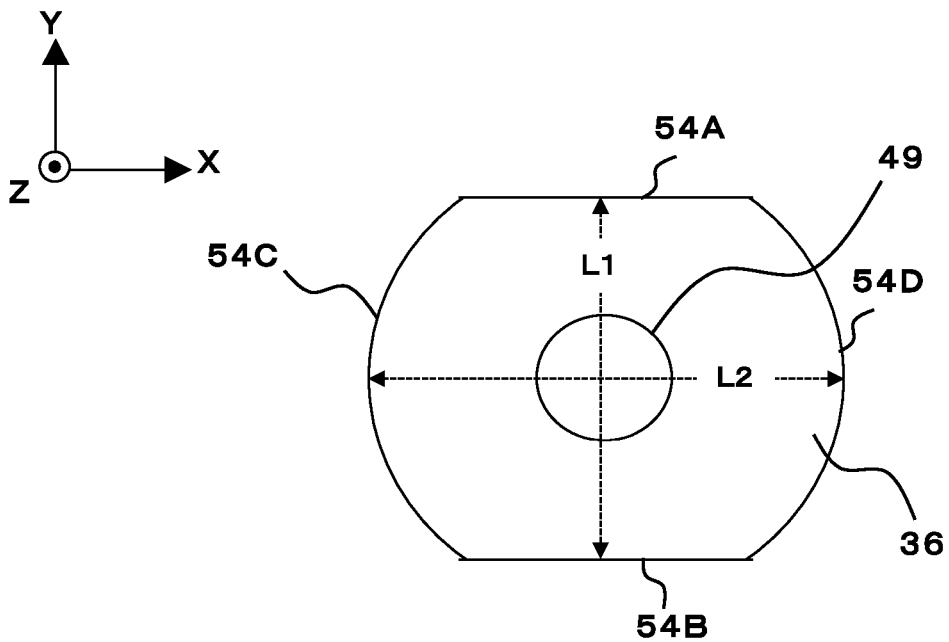
FIG. 9 illustrates a cross-sectional view of a cap member when viewed from a proximal end, according to one embodiment of the present disclosure.

FIG. 9 illustrates a cross-sectional view of an exemplary cap member 36 when viewed from the proximal end 21. That is, FIG. 9 illustrates a shape of the flat-plate portion of the cap member 36. In FIG. 9, X, Y, and Z axes corresponding to the X, Y, and Z axes shown in FIGS. 5 and 7 are shown. The Z-axis direction coincides with the first direction, and the X-axis direction and the Y-axis direction coincide with the second direction.

The flat-plate portion of the cap member 36 has a hole 49 communicating the aerosol flow path 48 and the aerosol discharge port 50. The shape of the flat-plate portion of the cap member 36 includes a first side 54A and a second side 54B that are substantially parallel to each other, a third side 54C that connects one end of the first side 54A and one end of the second side 54B, and a fourth side 54D that connects the other end of the first side 54A and the other end of the second side 54B. A distance L1 between the first side 54A and the second side 54B is shorter than a maximum distance L2 between the third side 54C and the fourth side 54D. The first side 54A and the second side 54B may be substantially linear. The third side 54C and the fourth side 54D may be substantially arcuate. This shape is merely an example of a shape of the flat-plate portion. The flat-plate portion may have various shapes such as a polygonal shape, which satisfy a relationship of L1<L2.

When L2/L1, which is the ratio of L2 to L1, is X, the relation of 0.1<X<2.0 may be preferably satisfied.

Figure 10:
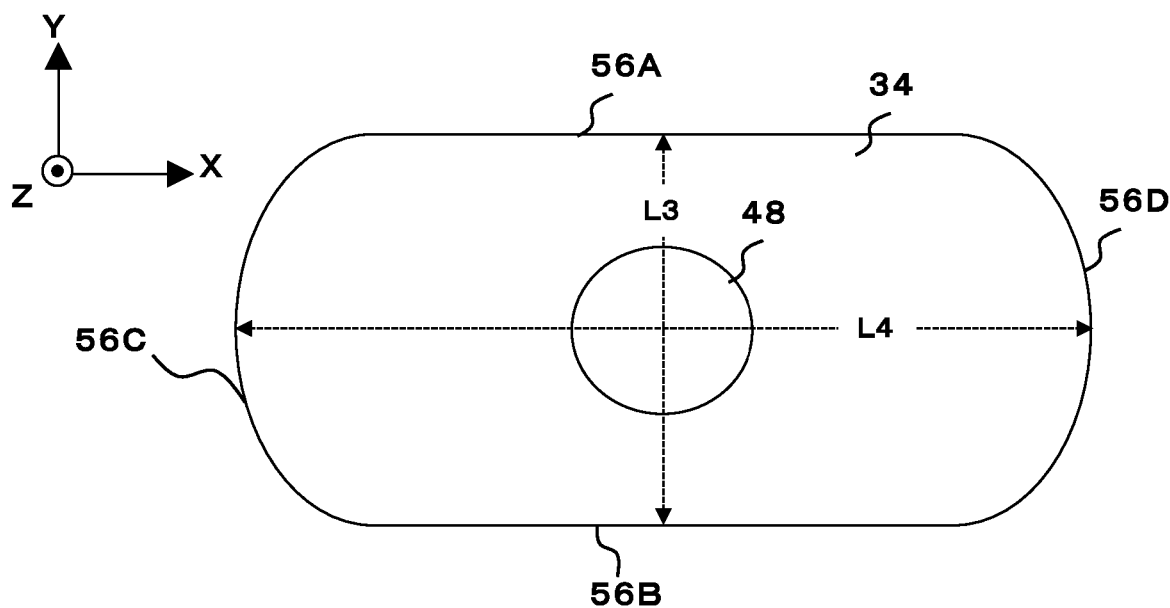
FIG. 10 illustrates an example of a shape formed by inside of a side wall of a tank body when viewed from the proximal end.

FIG. 10 illustrates a shape formed by the inside of the side wall of the tank body 34 when viewed from the proximal end 21. In FIG. 10, X, Y, and Z axes corresponding to the X, Y, and Z axes shown in FIG. 9 are shown. In addition, FIG. 10 illustrates a cross section of the aerosol flow path 48. The aerosol flow path 48 communicates with the aerosol discharge port 50 provided in the cover member 14, through the hole 49 provided in the flat-plate portion of the cap member 36.

The shape formed by the inside of the side wall of the tank body 34 when viewed from the proximal end 21 includes a fifth side 56A that is substantially parallel to the first side 54A illustrated in FIG. 9, a sixth side 56B that is substantially parallel to the second side 54B illustrated in FIG. 9, a seventh side 56C that connects one end of the fifth side 56A and one end of the sixth side 56B, and an eighth side 56D that connects the other end of the fifth side 56A and the other end of the sixth side 56B. A distance L3 between the fifth side 56A and the sixth side 56B is shorter than a maximum distance L4 between the seventh side 56C and the eighth side 56D. The shape illustrated in FIG. 10 is merely an example, and may be various shapes, which satisfy a relationship of L3<L4.

When L4/L3, which is the ratio of L4 to L3, is Y, the relation of 1.5<Y<3.5 may be preferably satisfied.

Figure 11:
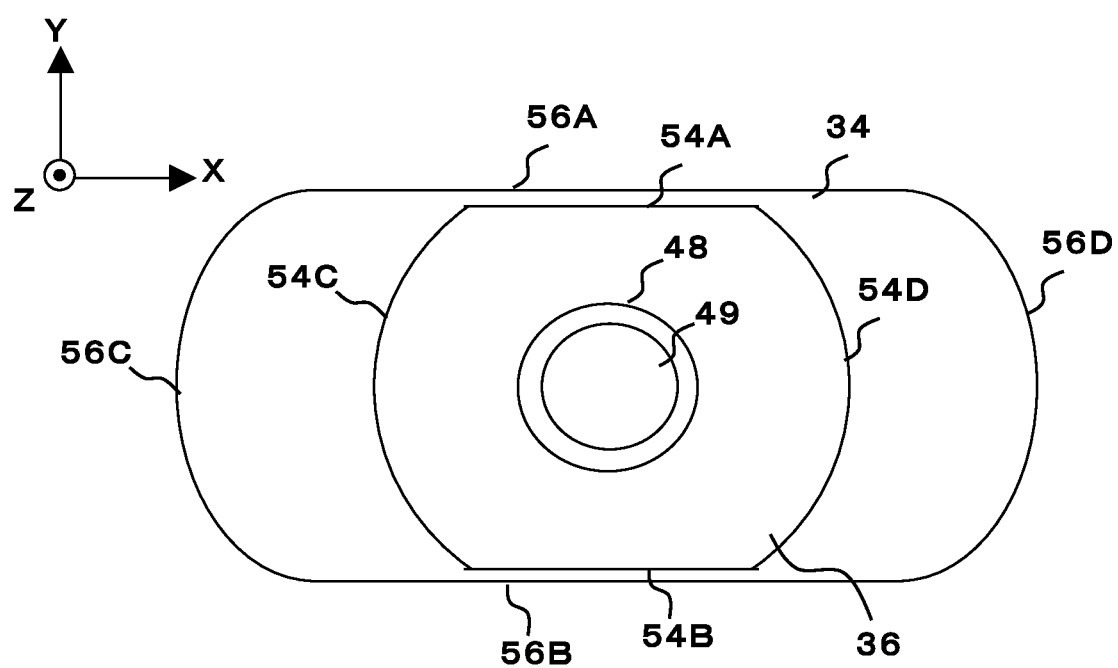
FIG. 11 illustrates an example of an arrangement relationship between the tank body and the cap member when viewed from the proximal end, in the cartridge according to one embodiment of the present disclosure.

FIG. 11 illustrates an example of an arrangement relationship between the tank body 34 and the cap member 36 when viewed from the proximal end 21, in the completed cartridge 20. A cross-sectional area of the hole 49 of the cap member 36 is smaller than the cross-sectional area of the aerosol flow path 48. The cap member 36 is arranged so that the first side 54A and the second side 54B illustrated in FIG. 9 face the fifth side 56A and the sixth side 56B illustrated in FIG. 10, respectively. The third side 54C and the fourth side 54D illustrated in FIG. 9 face the seventh side 56C and the eighth side 56D illustrated in FIG. 10, respectively.

As described above, the cap member 36 according to the present embodiment has a characteristic shape as illustrated in FIG. 9. When the flat-plate portion of the cap member 36 has a simple circle shape unlike in the present embodiment, the deformation of the cap member 36 caused when the cover member 14 and the tank body 34 are fitted with each other causes deformation of the shape of the hole in the cap member 36, which may cause inhibition of air flow communication between the aerosol flow path 48 and the aerosol discharge port 50 or leakage of the liquid from the tank 37 to the aerosol flow path 48. In contrast, using the cap member 36 according to the present embodiment makes it difficult to deform the shape of the cap member 36 even when the cover member 14 and the tank body 34 are fitted with each other, whereby the above-described problem can be prevented.

Hereinafter an operation of the inhaler 10 provided with the cartridge 20 of the present disclosure will be described. The liquid stored in the tank 37 contacts the end of the liquid holding member 26 which is exposed to the inside of the tank 37 and is absorbed by the liquid holding member 26. The absorbed liquid is transported to the part of the liquid holding member 26 which is exposed to the inside of the chamber 46 and is transported to the vicinity of the heater 32, utilizing capillary force. When the user inhales air through the aerosol discharge port 50, an air pressure sensor (not illustrated) provided in the battery unit 12 detects the inhalation, for example. In response to such detection, the electric power is supplied from the battery unit 12 to the heater 32. Therefore, the liquid held in the liquid holding member 26 is heated by the heater 32, and the liquid is atomized to generate the aerosol. The air having flowed into the cartridge 20 through the air inlet ports 35 in response to the user's inhalation passes through the aerosol flow path 48 and the aerosol discharge port 50, along with the aerosol generated in the chamber 46, and reaches the inside of the mouth of the user.

In the cartridge 20 according to the embodiment of the present disclosure, the heater 32 is mounted only on the first surface 27 of the liquid holding member 26. Thus, when the heater 32 is energized, the aerosol is generated preferentially on the aerosol discharge port 50 side. Accordingly, since the direction of generating the aerosol when the heater 32 is energized coincides with the direction of air flow caused by the inhalation, the frequency of contact between the generated aerosol and the wall surface forming the flow path can be reduced to thereby reduce condensation of the aerosol on the wall surface of the chamber 46.

When the liquid holding member 26 is formed of a fibrous member having flexibility, the liquid holding member 26 expands when holding the liquid. In the cartridge 20 of the present embodiment, the first surface 27 of the liquid holding member 26 may have a ridge shape. When the liquid holding member 26 has the ridge-shaped surface 27, an expansion amount of the ridge-shaped surface 27 in the protruding direction (Z-axis direction) is smaller than that when the liquid holding member 26 is flat. In other words, when the liquid holding member 26 is flat, the contact with the heater 32 may become unstable due to the expansion amount in the Z-axis direction when the liquid holding member 26 holds the liquid. In this case, the atomization efficiency of the liquid may be reduced. In contrast, in the cartridge 20 of the present embodiment in which the liquid holding member 26 has the ridge-shaped surface 27, a positional relationship between the liquid holding member 26 and the heater 32 is hardly changed between before and after the liquid is held. Accordingly, according to the cartridge 20 of the present embodiment, the positional relationship between the liquid holding member 26 and the heater 32 can be maintained at a desired degree as compared with the case where the liquid holding member 26 is flat. As a result, the liquid held in the liquid holding member 26 can be appropriately atomized.

When being energized, the heater 32 thermally expands due to an increase in temperature. In the cartridge 20 of the present embodiment, the heater 32 is curved along the ridge-shaped surface 27 of the liquid holding member 26 to thereby contact the ridge-shaped surface 27. When the heater 32 is curved, the position of the heater 32 in the protruding direction of the ridge-shaped surface 27 is hardly changed when the heater 32 thermally expands, as compared with the case where the heater 32 is substantially linear. Since the heater 32 of the present embodiment is curved, the position of the heater 32 in the protruding direction of the ridge-shaped surface 27 is hardly changed even when the heater 32 thermally expands, whereby the contact between the liquid holding member 26 and the heater 32 can be maintained.

Although the embodiments of the present disclosure have been described above, the present disclosure is not limited to the aforementioned embodiments and various modifications may be made within the scope of the technical idea described in the claims, the specification, or the drawings. Note that, any shape or material not directly described in the specification or the drawings falls within the scope of the technical idea of the present disclosure insofar as the shape or material provides an operation and effect of the present disclosure. For example, in the cartridge 20 of the embodiment, each component can be replaced, and such an embodiment also falls within the scope of the technical idea of the present disclosure.

REFERENCE SIGNS LIST

10 . . . Inhaler, 12 . . . Battery unit, 14 . . . Cover member, 16 . . . Tank unit, 17 . . . Heater unit, 18 . . . Charging unit, 20 . . . Cartridge, 21 . . . Proximal end, 22 . . . Base member, 23 . . . Distal end, 24 . . . Support member, 26 . . . Liquid holding member, 27 . . . First surface, 28 . . . Electrode holding member, 29 . . . Second surface, 30 . . . Electrode, 30A . . . First electrode, 30B . . . Second electrode, 31A-1, 31B-1 . . . First portion, 31A-2, 31B-2 . . . Second portion, 31A-3, 31B-3 . . . Third portion, 32 . . . Heater, 33A . . . First end part, 33B . . . Second end part, 34 . . . Tank body, 35A . . . First air inlet port, 35B . . . Second air inlet port, 36 . . . Cap member, 37 . . . Tank, 38 . . . Upper wall, 39B . . . Electrical contact, 40 . . . Side wall, 42 . . . Inner side wall, 44 . . . Chamber-forming member, 46 . . . Chamber, 48 . . . Aerosol flow path, 49 . . . Hole, 50 . . . Aerosol discharge port, 51 . . . Base, 52, 53 . . . Protrusion, 54A . . . First side, 54B . . . Second side, 54C . . . Third side, 54D . . . Fourth side, 56A . . . Fifth side, 56B . . . Sixth side, 56C . . . Seventh side, 56D . . . Eighth side, 58 . . . First convex surface, 60 . . . Second convex surface, 62 . . . First side portion, 64 . . . Second side portion, 88 . . . Center

The invention claimed is:

1. A cartridge for an inhaler, comprising:
a heater unit configured to atomize a liquid to generate aerosol,
wherein the heater unit includes:
  a liquid holding member that has a first surface, and a second surface opposite the first surface;
  a heater that contacts the first surface of the liquid holding member; and
  a support member that supports the second surface of the liquid holding member and is softer than the liquid holding member,
  wherein the heater is configured to press the liquid holding member against the support member.

2. The cartridge according to claim 1, wherein the first surface of the liquid holding member has a convex shape, and the support member has a first convex surface that supports the second surface of the liquid holding member.

3. The cartridge according to claim 2, wherein the support member further has a second concave surface opposite the first convex surface, a first side portion, and a second side portion facing the first side portion, and a space is formed by the second convex surface, an inner surface of the first side portion, and an inner surface of the second side portion.

4. The cartridge according to claim 1, further comprising:
a base member that holds at least a part of the support member and is harder than the support member.

5. The cartridge according to claim 4, wherein the base member has a base and holds the support member so that a space exists between the base and the support member.

6. The cartridge according to claim 4, wherein the base member has at least two first protrusions, and the at least two first protrusions contact an apex of the second convex surface.

7. The cartridge according to claim 6, wherein each of the at least two first protrusions also contacts the inner surface of the first side portion or the inner surface of the second side portion.

8. The cartridge according to claim 6, wherein the heater and the at least two first protrusions are arranged not to overlap each other when the heater unit is viewed from the base member side.

9. The cartridge according to claim 6, wherein the base member has at least two second protrusions, and the at least two second protrusions contact a portion below an apex of the second convex surface.

10. The cartridge according to claim 1, wherein the heater is a linear heater.

11. The cartridge according to claim 1, further comprising:
a tank unit that is to be engaged with the heater unit, wherein the tank unit is provided with:
  a tank body that has
  a tank for storing the liquid;
  an aerosol flow path which is separated from the tank and through which the aerosol passes; and
  a chamber communicating with the aerosol flow path,
  wherein a part of the liquid holding member and the heater are exposed to inside of the chamber, and another part of the liquid holding member is exposed to the inside of the tank.

* * * * *